(12) United States Patent
Fakhrzadeh et al.

(10) Patent No.: US 11,291,612 B2
(45) Date of Patent: Apr. 5, 2022

(54) INJECTABLE HYBRID CEMENT FOR DENTAL IMPLANTS AND METHODS OF MANUFACTURE THEREOF

(71) Applicant: Rutgers, The State University of New Jersey, New Brunswick, NJ (US)

(72) Inventors: Amir Fakhrzadeh, East Brunswick, NJ (US); Mohammad Ali Saghiri, Hackensack, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 143 days.

(21) Appl. No.: 16/790,202

(22) Filed: Feb. 13, 2020

(65) Prior Publication Data

US 2021/0169746 A1   Jun. 10, 2021

Related U.S. Application Data

(60) Provisional application No. 62/946,394, filed on Dec. 10, 2019.

(51) Int. Cl.

| | |
|---|---|
| *A61K 6/71* | (2020.01) |
| *A61K 6/17* | (2020.01) |
| *A61K 6/831* | (2020.01) |
| *A61K 6/853* | (2020.01) |
| *A61K 6/829* | (2020.01) |
| *A61K 6/84* | (2020.01) |
| *A61K 6/849* | (2020.01) |
| *A61K 6/851* | (2020.01) |
| *A61C 8/00* | (2006.01) |

(52) U.S. Cl.
CPC .............. *A61K 6/71* (2020.01); *A61C 8/0012* (2013.01); *A61K 6/17* (2020.01); *A61K 6/829* (2020.01); *A61K 6/831* (2020.01); *A61K 6/84* (2020.01); *A61K 6/849* (2020.01); *A61K 6/851* (2020.01); *A61K 6/853* (2020.01)

(58) Field of Classification Search
CPC .. A61C 8/0012; A61K 6/71849; A61K 6/853; A61K 6/851; A61K 6/829; A61K 6/84; A61K 6/831
See application file for complete search history.

(56) References Cited

U.S. PATENT DOCUMENTS

| | | | |
|---|---|---|---|
| 4,051,598 A | 10/1977 | Sneer | |
| 8,470,308 B2 * | 6/2013 | Wasielewski | ........ A61K 9/0009 424/93.1 |

(Continued)

OTHER PUBLICATIONS

Gurtu et al., "Evaluation of effect of dentin powder on antibacterial properties of Mineral Trioxide Aggregate—An in vitro study", Jun. 30, 2014, entire document, especially p. 120, paragraph 1, and p. 121, paragraph 6.

(Continued)

*Primary Examiner* — C Melissa Koslow
(74) *Attorney, Agent, or Firm* — Greenberg Traurig, LLP (57) ABSTRACT

A biomimetic composite material includes a bioactive cement material, an autologous dentin matrix, and an inorganic nano-reinforcement material. A dental implant includes a body including a biomimetic composite material, wherein the biomimetic composite material includes a bioactive cement material, an autologous dentin matrix, and an inorganic nano-reinforcement material.

20 Claims, 9 Drawing Sheets

(56) References Cited

U.S. PATENT DOCUMENTS

| | | |
|---|---|---|
| 2008/0090207 A1 | 4/2008 | Rubbert |
| 2010/0086618 A1 | 4/2010 | Pashlet et al. |
| 2010/0215617 A1 | 8/2010 | Wasielewski |
| 2012/0156308 A1 | 6/2012 | Lovschall et al. |
| 2013/0143179 A1 | 6/2013 | Um |

OTHER PUBLICATIONS

Graftys, "Grafty's Products" entire document, especially pp. 2-3.
Hilley et al., "Bioceramics in Endodontics", 2013, entire document.
Fontaine et al., "New calcium carbonate-based cements for bone reconstruction" Apr. 30, 2005, entire document, especially abstract, introduction, methods and materials.
Yakoob et al., "Evaluate the use of fresh Autogenous cement and dentine as bone graft to repair bone defects in dogs: experimental study", Jun. 30, 2006, entire document.
International Search Report and Written Opinion dated Nov. 1, 2018, issued by the U.S. Patent and Trademark Office in international application No. PCT/US2018/046515, 11 pages.
European Search Report for EP Application No. 18846032.3, dated Mar. 24, 2021, 8 pages.

\* cited by examiner

INJECTABLE HYBRID CEMENT FOR DENTAL IMPLANTS AND METHODS OF MANUFACTURE THEREOF

CROSS-REFERENCE TO RELATED APPLICATIONS

The present application is a § 111(a) application that claims priority to and the benefit of U.S. Provisional Patent Application Ser. No. 62/946,394, filed Dec. 10, 2019, the disclosure of which is herein expressly incorporated by reference in its entirety.

TECHNICAL FIELD

The present invention relates to the field of dentistry and more particularly, relates to customized dental implants that are formed of an injectable biomimetic composite material that is for the application of immediate tooth replacement.

BACKGROUND OF THE INVENTION

Titanium screw type dental implants are the current standard for replacing failing or missing natural teeth that require replacement due to tooth decay, periodontal disease, or trauma. The conventional process for placing standard dental implant involves a process where a hole is drilled into the bone and the implant device, typically made of titanium alloy (or other metal or ceramic material), is inserted (or threaded) into the cavity and allowed to fuse with the bone by a process known as osseointegration.

SUMMARY OF THE INVENTION

In accordance with some embodiments, the present disclosure is directed to a biomimetic composite material including a bioactive cement material; an autologous dentin matrix; and an inorganic reinforcement material.

In some embodiments, the bioactive cement material comprises a calcium silicate based dental cement.

In some embodiments the autologous dentin matrix comprises dentin particles.

In some embodiments, the inorganic reinforcement material comprises titanium.

In some embodiments, the inorganic reinforcement material comprises TI6AL4V.

In some embodiments, the inorganic reinforcement material is in the form of a foam.

In some embodiments, the inorganic reinforcement material is in the form of particles.

In some embodiments, the autologous dentin matrix comprises from 10 percent to 20 percent by weight of the biomimetic composite material.

In some embodiments, the inorganic reinforcement material comprises from 10 percent to 35 percent by weight of the biomimetic composite material.

In some embodiments, the ratio of bioactive cement material to autologous dentin matrix to reinforcement material is 1:1:3.

In some embodiments, the autologous dentin matrix comprises dentin particles with a particle size of 150 microns to 200 microns.

In some embodiments, the bioactive cement material comprises a mineral trioxide aggregate.

In accordance with some embodiments, the present disclosure is directed to a dental implant including a body including a biomimetic composite material, wherein the biomimetic composite material includes: 1) a bioactive cement material; 2) an autologous dentin matrix; and 3) an inorganic reinforcement material.

In some embodiments, the bioactive cement material comprises a calcium silicate based dental cement.

In some embodiments, the inorganic reinforcement material comprises titanium.

In some embodiments, the inorganic reinforcement material is in the form of a foam.

In some embodiments, the inorganic reinforcement material is in the form of particles.

In some embodiments, the autologous dentin matrix comprises dentin particles.

In some embodiments, the autologous dentin matrix comprises from 10 percent to 20 percent by weight of the biomimetic composite material.

In some embodiments, the inorganic reinforcement material comprises from 10 percent to 35 percent by weight of the biomimetic composite material.

In some embodiments, the autologous dentin matrix comprises dentin particles with a particle size of 150 microns to 200 microns.

In some embodiments, the ratio of bioactive cement material to autologous dentin matrix to reinforcement material is 1:1:3.

DETAILED DESCRIPTION OF THE INVENTION

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

For the following defined terms, these definitions shall be applied, unless a different definition is given in the claims or elsewhere in this specification.

As used herein, the term "proximal" is defined as a direction toward a user and the term "distal" is defined as a direction away from a user.

As used herein, the singular forms "a", "an", and "the" include plural referents unless the content clearly dictates otherwise. As used in this specification and the appended claims, the term "or" is generally employed in its sense including "and/or" unless the content clearly dictates otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

Although some suitable dimensions ranges and/or values pertaining to various components, features and/or specifications are disclosed, one of skill in the art, incited by the present disclosure, would understand desired dimensions, ranges and/or values may deviate from those expressly disclosed.

While dental implants are the current state of the art for tooth replacement, they involve an invasive surgical procedure and significant risks. Aside from intraoperative surgical risks, a high incidence of titanium implant failures is reported after placement due to a variety of reasons.

Often, when an implant fails, the amount of bone already lost or that needs to be removed in order to retrieve the titanium implant can be catastrophic and this makes replacing that implant extremely difficult, if not impossible. This bone loss leaves many patients debilitated and often times requires more extensive surgeries to compensate for the damage.

A major problem with these implants is that they are all a variation of the same screw type design and come in slightly different lengths, diameters, and surface modifications. In clinical practice, the occurrence of these variations translates to adjusting the patient to fit the needs of the implant rather than modifying the device to fit the needs of the patient.

The present disclosure relates to a novel biomimetic composite material for casting into dental implant molds or direct injection into fresh extraction sockets to create customizable dental implants for tooth replacement. In some embodiments, the biomimetic composite material includes a bioactive cement material, an autologous dentin matrix, and an inorganic reinforcement filler. In some embodiments, the composition and geometry of the autologous dentin matrix and the inorganic reinforcement filler is modified in order to increase the release of inorganic trace elements including Calcium and Strontium, as well as to improve the biological and mechanical properties of the biomimetic composite material.

Figure 1:
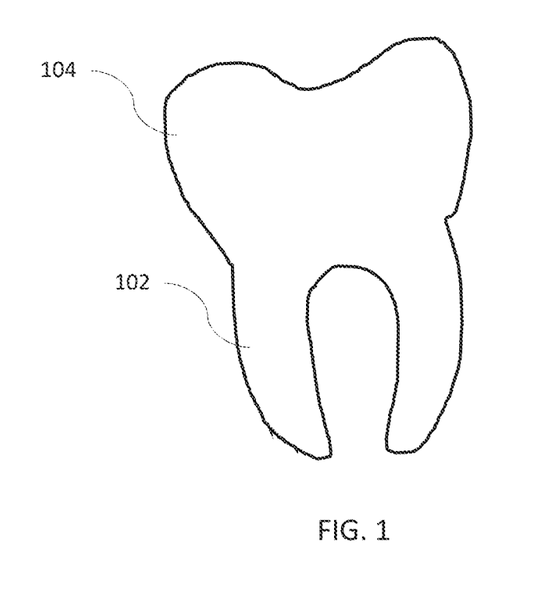
FIG. 1 is a cross-sectional view of an exemplary tooth.

As depicted in FIG. 1, the tooth is divided into two parts: (1) the root 102, which extends below the gum line and anchors the tooth into the bone; and (2) the crown 104, which is the visible, white part of the tooth. A human tooth includes four types of tissue, each performing a different function.

The first type of tooth tissue is enamel. Enamel is the visible substance that covers the crown of the tooth. Harder than bone, enamel protects the tooth from decay. Enamel is made up of phosphorous and calcium in a hydroxyapatite form, which is more mineralized than dentin and bone. They high hydroxyapatite content in enamel and natural teeth imparts strength and resistance to wear or breakdown.

The second type of tooth tissue is dentin. Dentin is the calcified layer just beneath the enamel. Dentin is also composed of calcium and phosphate and is harder than bone, but not as hard as enamel. Dentin makes up the majority of the crown and the roots of a tooth and is very similar in chemical composition to bone, except that it has a slightly higher mineral content. Dentin, like enamel, is composed of an organic (primarily collagen) matrix and an inorganic hydroxyapatite (calcium and phosphorous) component.

The third type of tooth tissue is cementum. Cementum covers the root dentin on one side and the periodontal ligament, which is attached to the surrounding alveolar bone, on the other side. There are two types of cementum: cellular and acellular. In some cases, cementum can be lost from the tooth in areas with disease or after mechanical debridement (e.g., by aggressive tooth brushing or from instrumentation at the dental office). Cementum does have the capacity at times to reform around the tooth after it has been lost, assuming that there is ample blood supply and that cementoblasts (cementum producing cells) are still present within the periodontal ligament space. The cementum, periodontal ligament and alveolar bone make up what is known as the Periodontium. The Periodontium retains teeth within the jawbone and is only present around natural teeth.

The fourth type of tooth tissue is pulp. Pulp is located at the center of the tooth and contains blood vessels, nerves and other soft tissues that deliver nutrients and signals to the tooth.

There are four types of teeth, each of which performs its own function. Incisors are the eight teeth in the front and center of the mouth (four on top and four on the bottom) that are designed to tear food apart in order to be chewed by the back teeth. Canines are the four sharpest teeth and are also used for ripping and tearing food apart. Premolars, or bicuspids, are used for chewing and grinding food. There are four premolars on each side of the mouth—two upper and two lower. Molars are the teeth found furthest back on both sides of the mouth. Molars are used for chewing and grinding food and often have multiple roots to withstand the highest chewing forces in the oral cavity. Each type of tooth also has its own shape. Thus, extraction sockets and tooth form implants are dictated by the type of tooth that is to be replaced.

The present disclosure relates to a biomimetic composite material including a bioactive cement material, an autologous dentin matrix, and an inorganic reinforcement filler that can be used to fill patient-specific extraction sockets and to form custom patient-specific tooth molds.

In some embodiments, the bioactive cement material includes a cement that is a mineral trioxide aggregate (MTA) that is mixed with water, calcium hydroxide (CH) and calcium silicate hydrate to form a calcium silicate cement (CSC). Calcium silicate cement releases calcium ions for cell attachment and proliferation, creates an antibacterial environment by its alkaline pH, and modulates cytokine production. In some embodiments, the bioactive cement material releases calcium to promote osteointegration. In some embodiments, the bioactive cement is Biodentine®, a CSC commercially available from Septodont. The mechanical properties of Biodentine® have been tailored to mimic natural human dentine and the product is marketed as "Dentin Replacement Material" due to its nearly identical physicochemical properties.

In some embodiments, a dual cement matrix is formed by mixing the bioactive cement material (e.g., Biodentine® material) and the autologous dentin matrix. In some embodiments, the autologous dentin matrix is a processed dentin material. Inclusion of the autologous dentin matrix in the bioactive cement material allows the biomimetic material to more closely replicate the properties of natural dentin. In some embodiments, the dentin material is from an extracted tooth from the patient, another human, or an animal donor/cadaver. In some embodiments, the dentin is from primary teeth (baby teeth) or permanent (wisdom teeth/premolars extracted for orthodontic purposes) teeth. Details of the processing of the dentin material are described below.

In some embodiments, the particle orientation and shape is variable. In some embodiments, the dentin particles may be flakelike, spherical or wedge shaped. In some embodiments, the particles are wedge-shaped with varying surface topography.

In some embodiments, the dentin particles have a particle size of 150 microns to 200 microns. In other embodiments, the dentin particles have a particle size of 160 microns to 200 microns. In other embodiments, the dentin particles have a particle size of 170 microns to 200 microns. In other embodiments, the dentin particles have a particle size of 180 microns to 200 microns. In other embodiments, the dentin particles have a particle size of 190 microns to 200 microns.

In some embodiments, the dentin particles have a particle size of 150 microns to 190 microns. In other embodiments, the dentin particles have a particle size of 150 microns to 180 microns. In other embodiments, the dentin particles have a particle size of 150 microns to 170 microns. In other embodiments, the dentin particles have a particle size of 150 microns to 160 microns.

In some embodiments, the dentin particles have a particle size of 160 microns to 190 microns. In other embodiments, the dentin particles have a particle size of 170 microns to 190 microns. In other embodiments, the dentin particles have a particle size of 180 microns to 190 microns. In other embodiments, the dentin particles have a particle size of 160 microns to 180 microns. In other embodiments, the dentin particles have a particle size of 170 microns to 180 microns. In other embodiments, the dentin particles have a particle size of 160 microns to 170 microns.

Once processed, the dentin particles taken from the tooth can be stored under dry conditions for use for the same patient. The dentin particulate can be stored in the office or in an offsite facility. More specifically, the dentin can be stored in: 1) either vacuum-sealed dry conditions or a designated freezer for short-term to long term storage in the dental office; 2) an offsite facility using long-term storage protocols (Schwartz 1986, IJOMS) which can be modified to replace human serum and tissue culture media with phosphate buffered saline (PBS) or distilled water; and/or 3) storage chambers that are specifically designed to house teeth in a manner that reduces microbial contamination or degradation of the material and allows for safe and stable transport and long term storage of the extracted tooth material.

The dual cement matrix including the bioactive cement material and the autologous dentin matrix is, in some embodiments, set by a hydration reaction. For example, in an embodiment, a calcium silicate cement reacts via a hydration based reaction and creates a calcium-silicate-hydrate (C-S-H) gel. The C-S-H gel is the most abundant reaction product, occupying about 80% of the paste volume and is responsible for most of the bioactive properties of the dual cement matrix. The setting of the dual cement matrix results in an extremely alkaline environment that can reach up to a pH of 11. One key feature of the present biomimetic composite material is that, unlike other cement systems, the biomimetic composite material maintains its insolubility in these highly alkaline environments without compromising biocompatibility or mechanical properties.

In some embodiments, the ratio of the bioactive cement material to the autologous dentin matrix is [100:1]. In other embodiments, the ratio of the bioactive cement to dentin is [90:1]. In other embodiments, the ratio of the bioactive cement to dentin is [80:1]. In other embodiments, the ratio of the bioactive cement material to the autologous dentin is [70:1]. In other embodiments, the ratio of the bioactive cement material to the autologous dentin is [60:1]. In other embodiments, the ratio of the bioactive cement material to the autologous dentin is [50:1]. In other embodiments, the ratio of the bioactive cement material to the autologous dentin is [40:1].

In some embodiments, an inorganic reinforcement material (reinforcement material) is incorporated into the bioactive cement material. The reinforcement material increases the compressive strength and improves the tensile strength of the bioactive cement material and the resulting biomimetic composite material. In some embodiments, the reinforcement material increases the mechanical properties of the biomimetic material from 50 Mpa to 800 Mpa. In other embodiments, the reinforcement material increases the mechanical properties of the biomimetic material from 100 Mpa to 800 Mpa. In other embodiments, the reinforcement material increases the mechanical properties of the biomimetic material from 200 Mpa to 800 Mpa. In other embodiments, the reinforcement material increases the mechanical properties of the biomimetic material from 300 Mpa to 800 Mpa. In other embodiments, the reinforcement material increases the mechanical properties of the biomimetic material from 400 Mpa to 800 Mpa. In other embodiments, the reinforcement material increases the mechanical properties of the biomimetic material from 500 Mpa to 800 Mpa. In other embodiments, the reinforcement material increases the mechanical properties of the biomimetic material from 600 Mpa to 800 Mpa. In other embodiments, the reinforcement material increases the mechanical properties of the biomimetic material from 700 Mpa to 800 Mpa.

In some embodiments, the reinforcement material increases the mechanical properties of the biomimetic material from 100 Mpa to 700 Mpa. In other embodiments, the reinforcement material increases the mechanical properties of the biomimetic material from 100 Mpa to 600 Mpa. In other embodiments, the reinforcement material increases the mechanical properties of the biomimetic material from 100 Mpa to 500 Mpa. In other embodiments, the reinforcement material increases the mechanical properties of the biomimetic material from 100 Mpa to 400 Mpa. In other embodiments, the reinforcement material increases the mechanical properties of the biomimetic material from 100 Mpa to 300 Mpa. In other embodiments, the reinforcement material increases the mechanical properties of the biomimetic material from 100 Mpa to 200 Mpa.

In some embodiments, the reinforcement material increases the mechanical properties of the biomimetic material from 200 Mpa to 700 Mpa. In other embodiments, the reinforcement material increases the mechanical properties of the biomimetic material from 300 Mpa to 600 Mpa. In other embodiments, the reinforcement material increases the mechanical properties of the biomimetic material from 400 Mpa to 500 Mpa. In other embodiments, the reinforcement material increases the mechanical properties of the biomimetic material from 500 Mpa to 700 Mpa. In other embodiments, the reinforcement material increases the mechanical properties of the biomimetic material from 300 Mpa to 600 Mpa. In other embodiments, the reinforcement material increases the mechanical properties of the biomimetic material from 200 Mpa to 400 Mpa.

In some embodiments, the reinforcement material is a bio-stable material that is stable during the hydration reaction of the dual cement matrix and after exposure to tissues and body fluid. The reinforcement material, in some embodiments, does not chemically react and agglomerate when in a solution and can easily and uniformly disperse during mixing and hydration. Another unique feature of the reinforcement material is the hydrophilicity thereof. Normally, metals and metal oxides are hydrophobic, which makes reproducibly obtaining a good mixture with the dual cement matrix challenging. In contrast, the present reinforcement material has increased wettability, as compared to other metals, and therefore is better suited for integration into the dual cement matrix during the hydration process. Additionally, the reinforcement material prevents the phenomena of stress shielding and stress concentration, two common causes of failure in conventional cements.

Exemplary reinforcement materials include, but are not limited to: titanium, titanium oxide, polypropylene, polystyrene, silk, or other materials.

In some embodiments, the reinforcement material is in the form of particles such as fibers, nano rods or needles.

In some embodiments, the particles are electrically charged and added to a fluid to prevent agglomeration thereof. In some embodiments, the particles have a length of 5 microns to 30 microns. In other embodiments, the particles have a length of 10 microns to 30 microns. In other embodiments, the particles have a length of 15 microns to 30 microns. In other embodiments, the particles have a length of 20 microns to 30 microns. In other embodiments, the particles have a length of 25 microns to 30 microns.

In some embodiments, the particles have a length of 5 microns to 25 microns. In other embodiments, the particles have a length of 5 microns to 20 microns. In other embodiments, the particles have a length of 5 microns to 15 microns. In other embodiments, the particles have a length of 5 microns to 10 microns.

In some embodiments, the particles have a length of 10 microns to 15 microns. In other embodiments, the particles have a length of 10 microns to 20 microns. In other embodiments, the particles have a length of 10 microns to 25 microns. In other embodiments, the particles have a length of 15 microns to 20 microns. In other embodiments, the particles have a length of 15 microns to 25 microns. In other embodiments, the particles have a length of 20 microns to 25 microns.

In some embodiments, the particles have a diameter of 1 micron to 10 microns. In other embodiments, the particles have a diameter of 2 microns to 10 microns. In other embodiments, the particles have a diameter of 4 microns to 10 microns. In other embodiments, the particles have a diameter of 6 microns to 10 microns. In other embodiments, the particles have a diameter of 8 microns to 10 microns.

In some embodiments, the particles have a diameter of 1 micron to 8 microns. In other embodiments, the particles have a diameter of 1 micron to 6 microns. In other embodiments, the particles have a diameter of 1 micron to 4 microns. In other embodiments, the particles have a diameter of 1 micron to 2 microns.

In some embodiments, the particles have a diameter of 2 microns to 8 microns. In other embodiments, the particles have a diameter of 6 microns to 8 microns. In other embodiments, the particles have a diameter of 4 microns to 6 microns. In other embodiments, the particles have a diameter of 2 microns to 4 microns. In other embodiments, the particles have a diameter of 4 microns to 8 microns.

Figure 2:
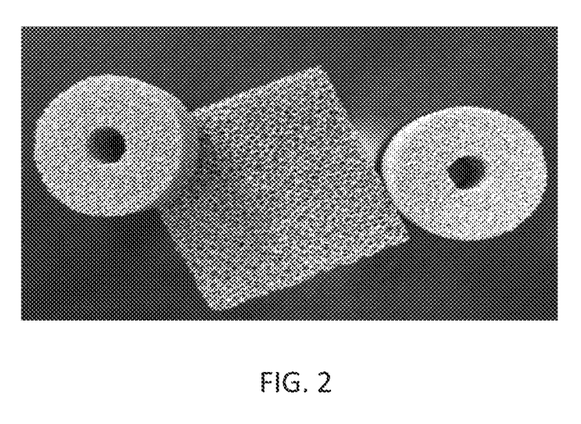
FIG. 2 is a perspective view of various exemplary titanium foams.
Figure 3:
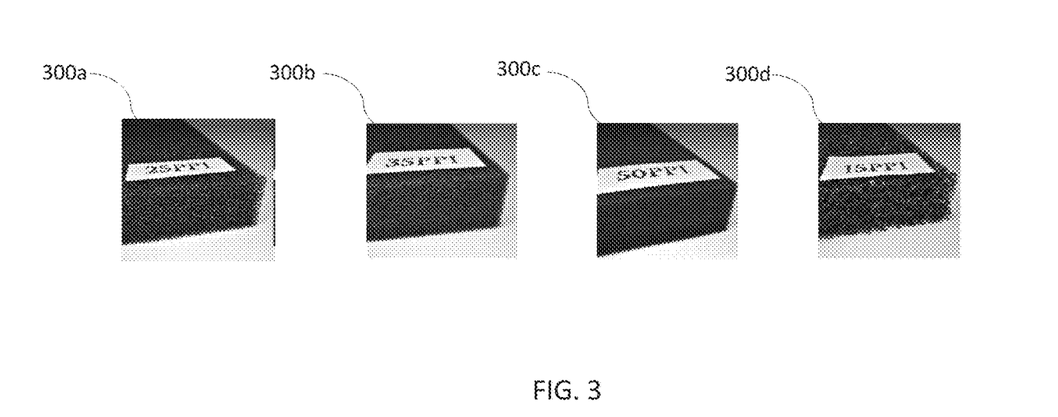
FIG. 3 is a cross-sectional view of four exemplary titanium foams according to exemplary embodiments of the present disclosure.
Figure 4:
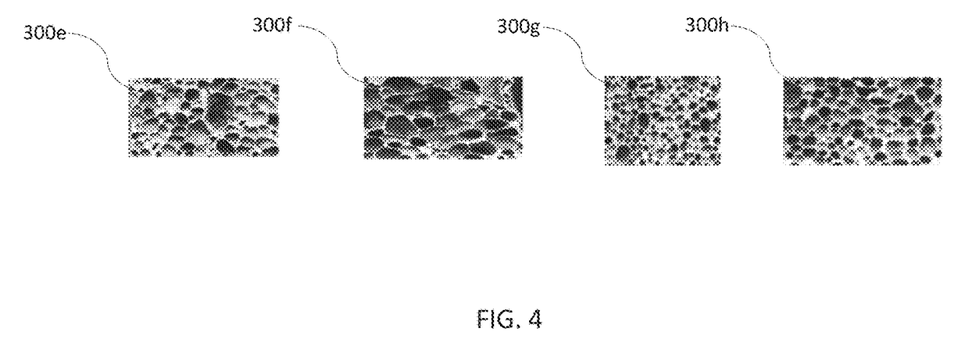
FIG. 4 is a cross-sectional view of a titanium foam mixed with a bioactive cement material according to exemplary embodiments of the present disclosure.

In other embodiments, the reinforcement material is in the form of a foam, as depicted in FIGS. 2-5. In some embodiments, the foam is trimmable, as will be described in further detail below. In some embodiments, the porosity and interconnectivity of the foam is important to ensure complete penetration of the dual cement matrix therethrough. In some embodiments, the level and type of porosity of the foam can be tailored based on the type of tooth or application. For example, FIGS. 2-5 depict various foams 300 that may be used. In some embodiments, the foam 300 can take various shapes such as, for example, ring or rectangular, as depicted in FIG. 2. In some embodiments, the foam may have various levels of pores per inch (PPI). FIG. 3 depicts a metal foams 300*a-d* having 25 PPI, 35 PPI, 50 PPI and 15 PPI, respectively. In some embodiments, the foam has a PPI of from 10 to 60. In other embodiments, the foam has a PPI of from 20 to 60. In other embodiments, the foam has a PPI of from 30 to 60. In other embodiments, the foam has a PPI of from 40 to 60. In other embodiments, the foam has a PPI of from 50 to 60.

In some embodiments, the foam has a PPI of from 10 to 50. In other embodiments, the foam has a PPI of from 10 to 40. In other embodiments, the foam has a PPI of from 10 to 30. In other embodiments, the foam has a PPI of from 10 to 20.

In some embodiments, the foam has a PPI of from 15 to 45. In other embodiments, the foam has a PPI of from 20 to 30. In other embodiments, the foam has a PPI of from 25 to 50. In other embodiments, the foam has a PPI of from 35 to 45. In other embodiments, the foam has a PPI of from 30 to 50.

As can be seen in FIG. 3, the porosity and porosity distribution of the foam may be varied as well. For example, the foams 300*e-f* have a lower porosity distribution (per centimeter) than foams 300*g-h*. To promote penetration of the dual cement matrix through the foam, in some embodiments, the foam has a porosity of 65% to 99%. In other embodiments, the foam has a porosity of 70% to 99%. In other embodiments, the foam has a porosity of 75% to 99%. In other embodiments, the foam has a porosity of 80% to 99%. In other embodiments, the foam has a porosity of 85% to 85%. In other embodiments, the foam has a porosity of 90% to 99%. In other embodiments, the foam has a porosity of 95% to 99%.

In some embodiments, the foam has a porosity of 65% to 95%. In other embodiments, the foam has a porosity of 65% to 90%. In other embodiments, the foam has a porosity of 65% to 85%. In other embodiments, the foam has a porosity of 65% to 80%. In other embodiments, the foam has a porosity of 65% to 75%. In other embodiments, the foam has a porosity of 65% to 70%.

In some embodiments, the foam has a porosity of 70% to 95%. In other embodiments, the foam has a porosity of 75% to 85%. In other embodiments, the foam has a porosity of 80% to 90%. In other embodiments, the foam has a porosity of 85% to 95%. In other embodiments, the foam has a porosity of 80% to 85%. In other embodiments, the foam has a porosity of 70% to 90%. In other embodiments, the foam has a porosity of 90% to 95%. In other embodiments, the foam has a porosity of 70% to 85%. In other embodiments, the foam has a porosity of 75% to 95%.

In some embodiments, the foam has a pore size of 5 µm to 1000 µm. In other embodiments, the foam has a pore size of 10 µm to 1000 µm. In other embodiments, the foam has a pore size of 50 µm to 1000 µm. In other embodiments, the foam has a pore size of 100 µm to 1000 µm. In other embodiments, the foam has a pore size of 250 µm to 1000 µm. In other embodiments, the foam has a pore size of 500 µm to 1000 µm. In other embodiments, the foam has a pore size of 750 µm to 1000 µm.

In some embodiments, the foam has a pore size of 5 µm to 750 µm. In other embodiments, the foam has a pore size of 5 µm to 500 µm. In other embodiments, the foam has a pore size of 5 µm to 250 µm. In other embodiments, the foam has a pore size of 5 µm to 100 µm. In other embodiments, the foam has a pore size of 5 µm to 50 µm. In other embodiments, the foam has a pore size of 5 µm to 10 µm.

Figure 5:
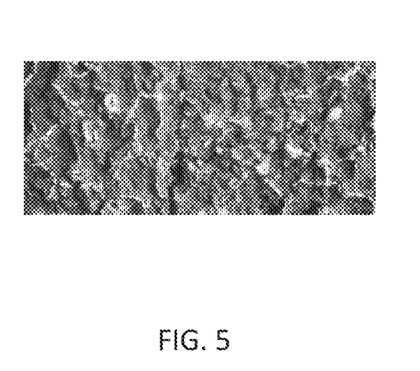
FIG. 5 is a cross-sectional view four exemplary titanium foams according to exemplary embodiments of the present disclosure.

In some embodiments, the foam has a pore size of 25 µm to 750 µm. In other embodiments, the foam has a pore size of 100 µm to 500 µm. In other embodiments, the foam has a pore size of 500 µm to 750 µm. In other embodiments, the foam has a pore size of 100 µm to 250 µm. In other embodiments, the foam has a pore size of 250 µm to 600 µm. In other embodiments, the foam has a pore size of 200 µm to 400 µm. FIG. 5 depicts a reinforcement material with the cement matrix incorporated therein.

In an exemplary embodiment, the reinforcement material is titanium. Titanium has favorable biocompatibility and physical properties. Furthermore, titanium is more resistant to dissolving in extreme conditions than other types of reinforcement material candidates. During the setting process, the pH of calcium silicate based cements can reach very alkaline (pH~11) levels. Such an alkaline pH will dissolve most types of materials dispersed into the cement material, creating small imperfections in the material. These imperfections inevitably result in weak points in the resulting composite material. Unlike most other materials, titanium and, in particular, the SLA-treated titanium alloys used herein, are able to form a protective $TiO_2$ layer when exposed to air. This $TiO_2$ layer serves as a protective surface coating and improves resistance to corrosion and solubility when the reinforcement material is exposed to the alkaline environment of the dual cement matrix.

In an embodiment, the titanium alloy is $TI_6AL_4V$. $TI_6AL_4V$ is an (α+β) titanium alloy that contains α stabilizer element Al and β stabilizer element V. Typically, the $TI_6AL_4V$ microstructure consists of transformed β containing acicular α as well as α at prior-β grain boundaries, while the annealed wrought $TI_6AL_4V$ bar typically consists of equiaxed α grain plus intergranular β.

In other embodiments, $TI_6AL_4V$ may be replaced with other titanium grades such as $Ti_6Al_7Nb$ and $Ti_5Al_{2-5}Fe$.

The relative amounts of the bioactive cement material to autologous dentin matrix to reinforcement material within the biomimetic composite material can vary depending upon the particular application and other considerations. For example, the autologous dentin matrix can comprise from about 10% by weight to about 20% by weight of the total biomimetic composite material. Additionally, the inorganic reinforcement material can comprise from about 10% by weight to about 35% by weight of the total biomimetic composite material. In an embodiment, the ratio of bioactive cement material to autologous dentin matrix to reinforcement material is 1:1:3.

In some embodiments, the biomimetic composite material includes at least one additive. Exemplary additives include, but are not limited to: strontium, magnesium, calcium, or phosphate ions. Strontium and magnesium are essential for bone formation and can be used as inorganic trace element additives. In some embodiments, strontium and magnesium are added to the biomimetic composite material via fluid used in the dual cement matrix hydration. In some embodiments, the fluid used for hydration is a water-based liquid or a gel containing either polyethylene glycol, alginate, or another polymer that has the capacity to produce a gel. Furthermore, the inclusion of metal ions such as calcium, magnesium and phosphate ions promote osteogenesis and angiogenesis, thus enhancing bone remodeling and repair processes.

It has been surprisingly found that the disclosed biomimetic composite materials perform very similarly to natural teeth when being prepared with any conventional dental rotary instruments. The biomimetic composite material is able to be machined and sectioned using diamond or carbide lathes, burs, and discs without unwanted discrimination or separation or the components therein. This good bonding of the bioactive cement material, the autologous dentin matrix and the reinforcement material ids due to the flow of the bioactive cement material into dentinal tubules and the reinforcement materials.

When compared to other implant materials, the disclosed biomimetic composite material is much closer in composition, color and mechanical properties, to a natural tooth. The biomimetic composite material mimics the mechanical properties of natural teeth in terms of mechanical strength and biocompatibility, and can be used as a dentin substitute due to its favorable long-term mechanical and antibacterial properties. The mechanical properties of the biomimetic composite materials disclosed herein are intended to be closer to the range of human dentin and bone than conventional implant materials. Specifically, the mismatch of material mechanical properties between conventional metal/zirconia screw type implants and the surrounding bone has been extensively documented in dental and orthopedic literature. The change in stress distribution from dynamic forces at the bone to implant interface, also known as stress shielding, is a significant issue that may contribute to high rates of implant failures. By matching the disclosed biomimetic composite material properties more closely to native tissues, the current disclosure provides a more natural distribution of multi-axial stresses results.

Manufacturing Methods

Figure 6:
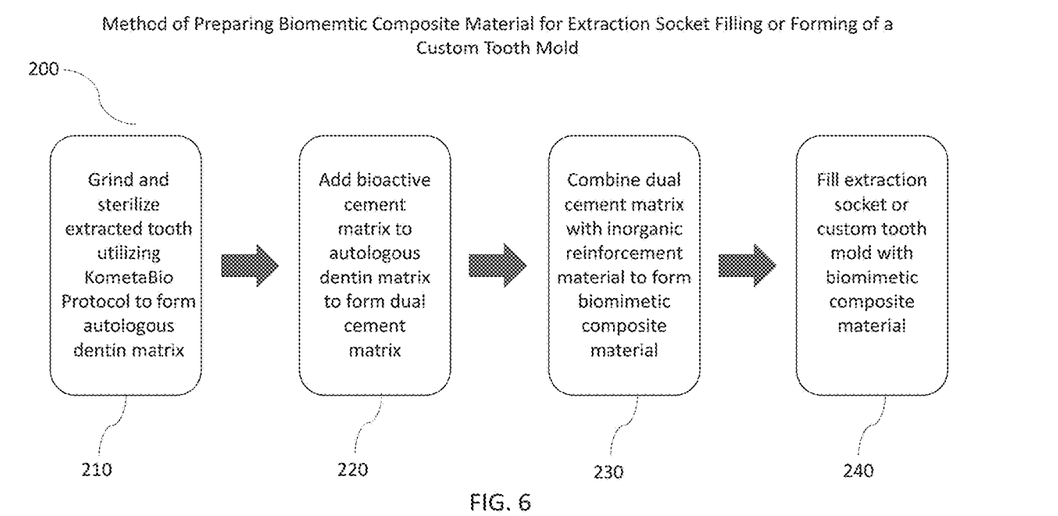
FIG. 6 is a flowchart setting forth the steps of an exemplary method of forming a biomimetic composite material according to exemplary embodiments of the present disclosure.

The above-described biomimetic material can be manufactured using any number of different suitable techniques. FIG. 6 illustrates a process for manufacturing the biomimetic composite material 200 in accordance with an exemplary embodiment of the present disclosure.

In step one 210, the autologous dentin matrix is formed by subjecting an extracted tooth to a process that grinds and sterilizes the extracted tooth. In some embodiments, dentin particles are produced from a tooth using a commercially available dentin grinder machine such as the Smart Dentin Grinder from Kometabio.

During the process, decay and filling material as well as the enamel and cementum is initially removed with a highspeed rotary bur. The tooth is then dried and placed into the dentin grinder machine, which grinds the tooth into small particles. The particles are collected in two chambers below the grinding cartridge and sterilized using a chemical sterilization process of NaOH and ethanol solution wash followed by multiple washes with a phosphate buffered solution and distilled water. The particles are then dried with sterile gauze and a hot plate, if needed.

The above-described protocol and equipment allows autologous dentin to be produced. By grinding the extracted tooth, dentin in particle form is produced and is subsequently used in making the biomimetic composite material.

In some embodiments, the dentin particles are treated with Vitamin C for 5-10 minutes prior to mixing with the bioactive cement material to prevent the dentin particles from dissolving during the high pH setting reaction of the bioactive cement material.

In step two 220, once the dentin is processed, the bioactive cement material is added to the autologous dentin matrix according to desired ratios to form the dual cement matrix. In some embodiments, other ingredients, such as water and additives, are added to the dual cement matrix. The materials are then mixed using conventional equipment, such as a dental triturator.

In one example, the mixing process includes the following steps:
1. 700.2 mg of dentin powder is added to 700 mg of cement powder in a capsule.
2. The capsule is placed in a dental triturator and mulled for 10 seconds to mix the two powder components.
3. The capsule is removed from the triturator and 7 drops of liquid from a pipette are added to the capsule.
4. The capsule is placed back in the triturator and triturated at a minimum speed of 4,000 rpm for 30 seconds.

In some embodiments, the dual cement matrix is chemically sterilized with injectable Ascorbic Acid [1:1].

In step three 230, once the dual cement matrix has been formed, it is combined with the reinforcement material prior to setting.

Figure 7:
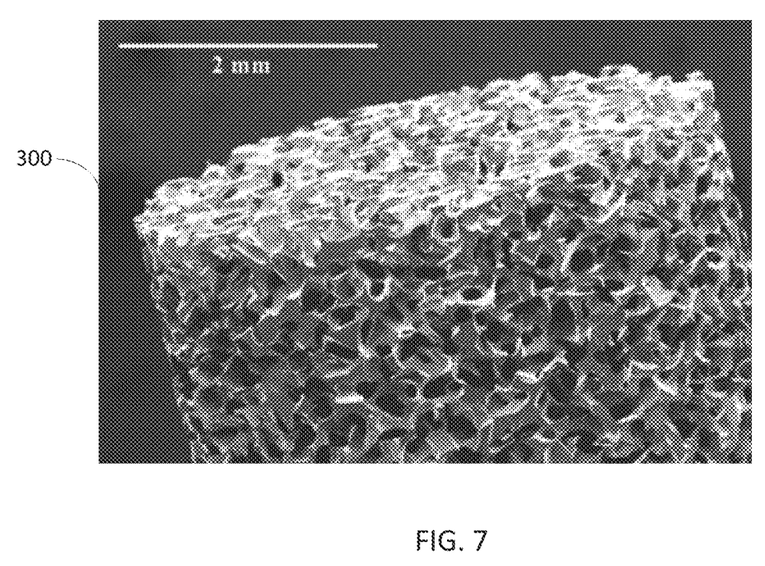
FIG. 7 is a view of a titanium foam reinforcement material according to an exemplary embodiment of the present disclosure.

In some embodiments, as described above, the reinforcement material is in the form of a prefabricated foam. In an exemplary embodiment, the foam is a titanium foam produced by a powder metallurgical process using a space holder method. An exemplary sample titanium foam 300 is depicted in FIG. 7. In one example, the titanium foam is produced according to the following steps:
1. Mixing of fine titanium powder with a space holder substance;
2. Pressing of a green body;
3. Removal of the space holder substance; and
4. Sintering.

In some embodiments, the titanium powder is a commercially pure (cp) titanium grade 4 according to the ASTM standard F1580-01. In some embodiments, the grain size of the titanium powder follows a log—normal distribution with an average d50-value of 25-40 µm. In some embodiments, the space holder substance is ammoniumhydrogencarbonate ($NH_4$)$HCO_3$, according to the British pharmacopoeia BP E503. In some embodiments, the desired grain size of the space holder particles (425-710 µm) is obtained by sieving. This grain size is chosen to achieve a final pore size in the approximate range of 100-500 µm, which is known to result in a consistent tissue response and rapid bone formation. In some embodiments, the total porosity of the titanium foam is adjusted to the range of 65-99% by adding an adequate amount of the space holder particles. The two powders are mixed in a proprietary process using tumbling glass bottles. The green bodies are pressed with two different compaction methods: cold-isostatic and uniaxial.

In some embodiments, the titanium foam is treated to increase wettability thereof. Because titanium foam is a hydrophobe, it is difficult to mix with the dual cement matrix and may not be distributed through some portions of the dual cement matrix. To increase wettability, in some embodiments, the titanium foam is grit-blasted and acid-etched to make the surface SLA, and further processed to a high degree of hydrophilicity. The protocol for the SLA treatment is previously described by Wennerberg. Acid attack of the surface of dental implants, as in SLA treatment, results in uniform roughness with pits and craters of micrometric size, leading to an increase in surface area. In these pits, osteoblasts and supportive connective tissue can migrate, resulting an enhancement in bioadhesion. In other embodiments, the wettability of the titanium foam is increased by other methods or treatments.

Each manufacturer has its own method of acid etching by controlling the temperature, concentration of acids, and exposure time. SLA implants are often used in clinical practice. One aim of the present disclosure is to determine a proper preparation technique for the surface of SLA dental implants, in the absence of detailed specification of manufacturing process of commercially available implants. By controlling the disclosed acid etching process with regard to mixture of acids used, concentration, temperature, exposure time, $Ti_6Al_4V$ dental implants with a moderately rough topography and good hydrophilic properties are obtained.

Figure 8:
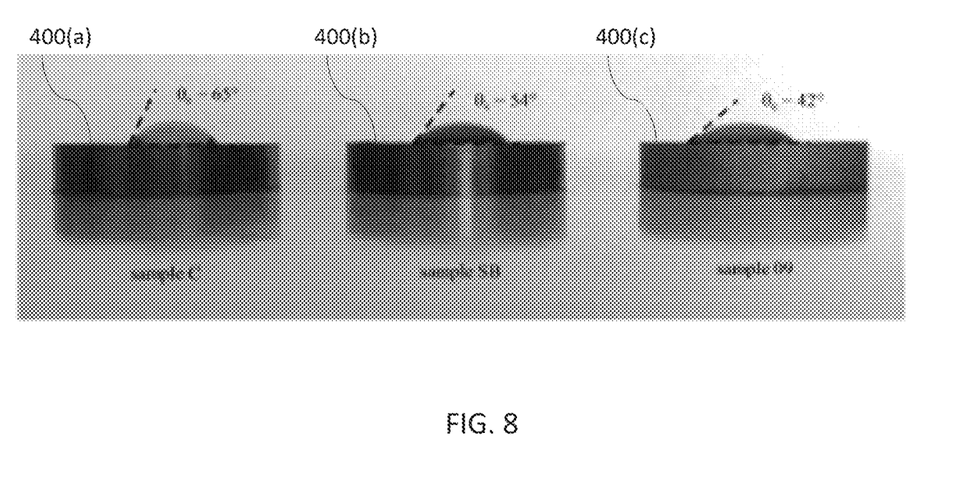
FIG. 8 is a perspective view of the wettability of a machined, sand blasted, and sand blasted and acid etched $Ti_6Al_4V$ surfaces.

Specifically, an exemplary protocol for increasing the wettability of titanium reinforcement materials, according to an embodiment of the present disclosure, includes subjecting the reinforcement material to acid etch using HCl In, $H_2SO_4$In, or a combination of HCl and $H_2SO_4$ (1:1). In some embodiments, the concentration of acid solution is 4.9% sulfuric acid and 3.65% hydrochloric acid. FIG. 8 depicts the wettability of a machined $Ti_6Al_4V$ surface 400(*a*), a sand blasted $Ti_6Al_4V$ surface 400(*b*), and a sand blasted and acid etched $Ti_6Al_4V$ surface 400(*c*) in increasing order from left to right.

Once the reinforcement foam is formed, it may be stored in synthetic tissue fluid. Before clinical application, the clinician can cut, shape and trim the foam to a desired shape. The reinforcement foam is then combined with the dual cement matrix and the resulting implant is placed in the tooth socket. In some embodiments, additional dual cement matrix is packed into the socket to ensure that the implant is intimately adapted to the tooth socket.

In other embodiments, as described above, the dual cement matrix is combined with a reinforcement material in the form of reinforcement particles. In these embodiments, the reinforcement material is prepared for in situ mixing with the cement matrix.

In some embodiments, the reinforcement material is in the form of titanium micro rods having a length of 200 to 500 µm and a diameter of 10 to 100 µm. The titanium micro rods can be prepared by various different methods such as, for example, electrospinning or mechanical grinding. Similar to the titanium foam reinforcement material, in some embodiments, the titanium micro rods are SLA treated to increase wettability thereof. Specifically, the same grit-blasting and acid-etching protocol described above may be used to increase the wettability of the micro rods.

Once the reinforcement particles are formed, they can be added to the dual cement matrix during mixing. In step four 240, the resulting paste may then be used to fill the extraction socket or in a custom patient specific tooth mold (described below).

Customized Tooth Form Implants

Figure 9:
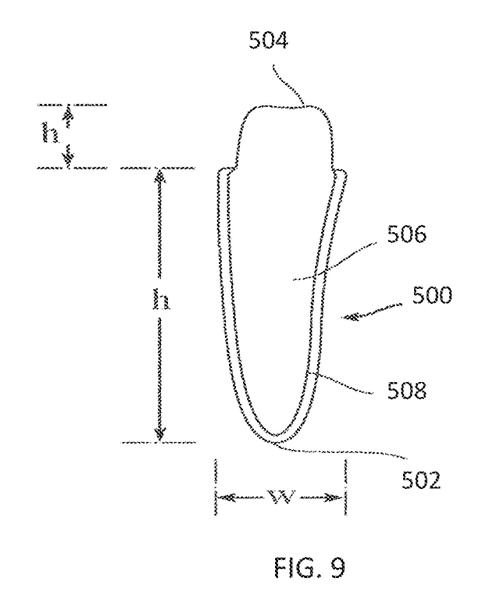
FIG. 9 is a cross-sectional view of a tooth form implant in the form of an incisor/canine implant according to exemplary embodiments of the present disclosure.

FIG. 9 depicts a tooth form implant 500 in the form of an incisor/canine tooth implant, according to an embodiment of the present disclosure. The implant 500 has a root portion 502 and a crown portion 504. As described herein, the implant 500 is constructed in view of the anatomy of a patient and in particular, the size and shape of the implant 500 is intended to mimic an extracted or otherwise missing tooth. In some embodiments, the implant 500 includes a core 506 and an outer layer 508 surrounding the core 506. In some embodiments, the outer layer 508 covers an entire surface area of the core 506. In other embodiments, the outer layer 508 covers a portion of the surface area of the core 506. In some embodiments the core 506 is formed of a first material while the outer layer 508 is formed of a second material that is different than the first material.

In some embodiments, a thickness of the core 506 is greater than a thickness of the outer layer 508. As defined herein, a "thickness" is a dimension between two lateral surfaces of the component. In some embodiments, the thickness of the core 506 is from 1 mm to 10 mm. In some embodiments, a thickness of the outer layer 508 is from 500 µm to 1500 µm.

In some embodiments, the core 506 and the outer layer 508 comprise the biomimetic composite material disclosed herein. In some embodiments, the core 506 and the outer layer 508 comprise the biomimetic composite material with different ratios of the bioactive cement material, autologous dentin matrix and inorganic reinforcement fiber. In other embodiments, the core 506 and the outer layer 508 comprise the biomimetic composite material with the same ratio of the bioactive cement material, autologous dentin matrix and inorganic reinforcement fiber.

While various embodiments of the present disclosure have been described above, it should by understood that the embodiments have been presented by way of example, and not limitation. Thus, various changes in form and detail could be made therein without departing from the spirit and scope of the disclosure. Accordingly, the present invention should not be limited by any of the above-described exemplary embodiments, but should be defined only in accordance with the following claims and their equivalents.

What is claimed is:

1. A biomimetic composite material comprising:
   1) a bioactive cement material;
   2) an autologous dentin matrix; and
   3) an inorganic reinforcement material.

2. The biomimetic composite material of claim 1, wherein the bioactive cement material comprises a calcium silicate based dental cement.

3. The biomimetic composite material of claim 1, wherein the autologous dentin matrix comprises dentin particles.

4. The biomimetic composite material of claim 1, wherein the inorganic reinforcement material comprises titanium.

5. The biomimetic composite material of claim 1, wherein the inorganic reinforcement material comprises $TI_6AL_4V$.

6. The biomimetic composite material of claim 1, wherein the inorganic reinforcement material is in the form of a foam.

7. The biomimetic composite material of claim 1, wherein the inorganic reinforcement material is in the form of particles.

8. The biomimetic composite material of claim 1, wherein the autologous dentin matrix comprises from 10 percent to 20 percent by weight of the biomimetic composite material.

9. The biomimetic composite material of claim 1, wherein the inorganic reinforcement material comprises from 10 percent to 35 percent by weight of the biomimetic composite material.

10. The biomimetic composite material of claim 1, wherein the ratio of bioactive cement material to autologous dentin matrix to reinforcement material is 1:1:3.

11. The biomimetic composite material of claim 1, wherein the autologous dentin matrix comprises dentin particles with a particle size of 150 microns to 200 microns.

12. The biomimetic composite material of claim 1, wherein the bioactive cement material comprises a mineral trioxide aggregate.

13. A dental implant comprising:
   a body comprising a biomimetic composite material,
      wherein the biomimetic composite material comprises:
         1) a bioactive cement material;
         2) an autologous dentin matrix; and
         3) an inorganic reinforcement material.

14. The dental implant of claim 13, wherein the bioactive cement material comprises a calcium silicate based dental cement.

15. The dental implant of claim 13, wherein the inorganic reinforcement material comprises titanium.

16. The dental implant of claim 13, wherein the inorganic reinforcement material is in the form of a foam.

17. The dental implant of claim 13, wherein the inorganic reinforcement material is in the form of particles.

18. The dental implant of claim 13, wherein the autologous dentin matrix comprises dentin particles.

19. The dental implant of claim 13, wherein the autologous dentin matrix comprises from 10 percent to 20 percent by weight of the biomimetic composite material.

20. The dental implant of claim 13, wherein the inorganic reinforcement material comprises from 10 percent to 35 percent by weight of the biomimetic composite material.

* * * * *